(12) United States Patent
Saitoh et al.

(10) Patent No.: US 9,221,823 B2
(45) Date of Patent: *Dec. 29, 2015

(54) CRYSTAL FORM OF PYRROLIDYLTHIOCARBAPENEM DERIVATIVE

(71) Applicant: Shionogi & Co., Ltd., Osaka (JP)

(72) Inventors: Izumi Saitoh, Amagasaki (JP);
Masayuki Takahira, Amagasaki (JP);
Toshio Kawakita, Amagasaki (JP);
Yasuyuki Yoshioka, Amagasaki (JP)

(73) Assignee: SHIONOGI & CO., LTD., Osaka-Shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/187,010

(22) Filed: Feb. 21, 2014

(65) Prior Publication Data

US 2015/0031664 A1    Jan. 29, 2015

Related U.S. Application Data

(63) Continuation of application No. 13/585,611, filed on Aug. 14, 2012, now abandoned, which is a continuation of application No. 12/012,932, filed on Feb. 5, 2008, now Pat. No. 8,247,402, which is a continuation of application No. 11/595,348, filed on Nov. 10, 2006, now abandoned, which is a continuation of application No. 10/240,465, filed as application No. PCT/JP01/02834 on Mar. 30, 2001, now abandoned.

(30) Foreign Application Priority Data

Mar. 31, 2000  (JP) ................. 2000-099868

(51) Int. Cl.
*C07D 477/20*    (2006.01)

(52) U.S. Cl.
CPC ........... *C07D 477/20* (2013.01); *C07B 2200/13* (2013.01)

(58) Field of Classification Search
CPC .................................................. C07D 477/20
USPC ..................... 540/350; 514/210.12
See application file for complete search history.

(56) References Cited

U.S. PATENT DOCUMENTS

| | | | |
|---|---|---|---|
| 5,317,016 A | 5/1994 | Nishitani et al. | |
| 6,111,098 A | 8/2000 | Inoue et al. | |
| 8,247,402 B2 * | 8/2012 | Saitoh et al. | 514/210.12 |
| 2006/0229285 A1 | 10/2006 | Uenaka | |
| 2012/0035357 A1 | 2/2012 | Kanagaraj et al. | |

FOREIGN PATENT DOCUMENTS

| | | |
|---|---|---|
| CN | 1151162 | 6/1997 |
| EP | 0557122 | 8/1993 |
| JP | 5-294970 | 11/1993 |
| JP | 08012674 | 1/1996 |
| WO | WO 95/29913 | 8/1993 |

OTHER PUBLICATIONS

Iso et al., "A novel 1β-methylcarbapenem antibiotic", S-4661, The Journal of Antibiotics, 49(2), 199-209 (1996).
Iso et al., Synthesis and Modification of a Novel 1β-Methyl Carbapenem Antibiotic, S-4661, 49(5), 478-484 (1996).
Kume, et al., "Efficient and practical synthesis of 1β-methylcarbapenems", Tetrahedron, 53(5), 1635-1646 (1997).
Notice of Certificate under 21 U.S.C. §355(j)(2)(B) (§505(j)(2)(B)) of Federal Food, Drug and Cosmetic Act) and 21 C.F.R. §314.95, Nov. 14, 2012.
Yvon et al., "Lazy Pulverix, a computer program, for calculating X-ray and neutron diffraction powder patterns," J. Appl. Cryst. (1977). 10, 73-74.
Antibotic Technology, edited by Yu Wenhe, Yang Jigen, Liaoning Science and Technology Press, published Sep. 1988.
Organic Chemistry Experiments (Edition 2), edited by Huang Tao, Higher Education Press, published May 1999.
Pharmacopoeia of the People's Republic of China 2000 Edition, vol. II, edited by Chinese Pharmacopoeia Commission, Chemical Industry Press, published Jan. 2000.

* cited by examiner

*Primary Examiner* — Golam M M Shameem
(74) *Attorney, Agent, or Firm* — Ropes & Gray LLP; James F. Haley, Jr.; Yang Xu

(57) ABSTRACT

Novel crystals of a pyrrolidylthiocarbapenem derivative having excellent stability is provided. According to the present invention, a crystal of (+)-(4R,5S,6S)-6-[(1R)-1-hydroxyethyl]-4-methyl-7-oxo-3[[(3S,5S)-5-(sulfamoylaminomethyl)pyrrolidin-3-yl]thio]-1-azabicyclo[3.2.0]hept-2-ene-2-carboxylic acid having a diffraction pattern in powder X-ray diffraction having main peaks at diffraction angles (2θ) of about 6.62, 13.04, 15.44, 16.58, 17.64, 20.88, 23.26, 25.02 and 25.52 (degrees) are provided.

3 Claims, 5 Drawing Sheets

CRYSTAL FORM OF PYRROLIDYLTHIOCARBAPENEM DERIVATIVE

CROSS-REFERENCE TO RELATED APPLICATIONS

This application is a continuation of U.S. patent application Ser. No. 13/585,611, filed Aug. 14, 2012, which is a continuation of U.S. patent application Ser. No. 12/012,932, filed Feb. 5, 2008 (now U.S. Pat. No. 8,247,402), which is a continuation of U.S. patent application Ser. No. 11/595,348, filed Nov. 10, 2006 (now abandoned), which is a continuation of U.S. patent application Ser. No. 10/240,465, filed Sep. 30, 2002 (now abandoned), which is a national stage application under 35 U.S.C. §371 of International Application PCT/JP01/02834, filed Mar. 30, 2001, which application claims priority from Japanese Application 2000-99868, filed Mar. 31, 2000. The disclosure of each of these referenced applications is incorporated by reference herein in its entirety.

TECHNICAL FIELD

The present invention relates to a novel pyrrolidylthiocarbapenem derivative crystal and a method for producing the same.

BACKGROUND ART

The compound (+)-(4R,5S,6S)-6-[(1R)-1-hydroxyethyl]-4-methyl-7-oxo-3[[(3S,5S)-5-(sulfamoylaminomethyl)pyrrolidin-3-yl]thio]-1-azabicyclo[3.2.0]hept-2-ene-2-carboxylic acid (hereinafter simply referred to as S-4661) having a structure represented by the formula below is a pyrrolidylthiocarbapenem derivative, which is a useful compound as an antimicrobial drug.

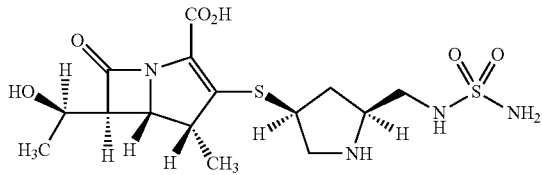

(Formula 1)

Note that this compound is also designated as "(4R,5S,6S)-3-[[(3S,5S)-5-(sulfamoylaminomethyl)pyrrolidin-3-yl]thio]-6-[(1R)-1-hydroxyethyl]-4-methyl-7-oxo-1-azabicyclo[3.2.0].hept-2-ene-2-carboxylic acid" or "(1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid".

S-4661 is described in Japanese Laid-Open Publication No. 5-294970. However, Japanese Laid-Open Publication No. 5-294970 describes only examples in which an amorphous form thereof was isolated. The amorphous solid of S-4661 has insufficient stability in storage, so that long-term storage under typical storage conditions disadvantageously leads to discoloration and a reduction in purity. Therefore, in order to develop S-4661 as a medicament, particularly an injection, a crystalline preparation having higher storage stability as compared to amorphous preparations is desired.

For this reason, a variety of crystals of S-4661 have been studied for improvements in storage stability, ease of handling, and the like of S-4661. As a result, a variety of crystals of S-4661 were confirmed.

For example, JP No. 2843444 discloses a type I crystal and a type II crystal of S-4661. The peaks of the type I crystal and type II crystal have characteristic diffraction angles (2θ) in X-ray diffraction as follows:

Type I: 7.32, 14.72, 18.62, 20.42, 21.1, 22.18, 23.88, and 29.76 (degrees) and

Type II: 6.06, 12.2, 14.56, 17.0, 18.38, 20.68, 24.38, 24.60, 25.88, and 30.12 (degrees)

(conditions for measurement of X-ray diffraction: CuKα ray, 1.54 Angstroms (monochromator), tube voltage 40 kV, tube current 40 mA).

However, in the art, a still further improvement in the stability of S-4661 has been desired.

Problems to be Solved by the Invention

The present invention solves the above-described conventional problems. An object of the present invention is to provide a novel crystal having excellent storage stability, good ease of handling and the like, and a method for producing the same.

Another object of the present invention is to provide a novel crystal applicable to a powder filling preparation and a method for producing the same.

DISCLOSURE OF THE INVENTION

Means for Solving the Problems (1) According to the present invention, a crystal of (+)-(4R,5S,6S)-6-[(1R)-1-hydroxyethyl]-4-methyl-7-oxo-3[[(3S,5S)-5-(sulfamoylaminomethyl)pyrrolidin-3-yl]thio]-1-azabicyclo[3.2.0]hept-2-ene-2-carboxylic acid having a diffraction pattern in powder X-ray diffraction having main peaks at diffraction angles (2θ)=13.04, 14.98, 15.88, 16.62, 20.62, 21.06, 22.18, 23.90, 26.08, 28.22 and 28.98 (degrees), or a hydrate thereof, is provided.

(2) According to the present invention, a medicament containing the crystal of (1) is provided.

(3) In one embodiment, the medicament of (2) is an injection.

(4) In one embodiment, the medicament of (2) is a powder filling preparation.

(5) According to the present invention, a crystal of (+)-(4R,5S,6S)-6-[(1R)-1-hydroxyethyl]-4-methyl-7-oxo-3[[(3S,5S)-5-(sulfamoylaminomethyl)pyrrolidin-3-yl]thio]-1-azabicyclo[3.2.0]hept-2-ene-2-carboxylic acid having a diffraction pattern in powder X-ray diffraction having main peaks at diffraction angles (2θ)=6.78, 6.96, 15.74, 17.92, 21.16, 23.56, and 25.80 (degrees), or a hydrate thereof, is also provided.

(6) In one aspect, a method according to the present invention is a method for producing the crystal of (5), comprises the steps of:

(A) dissolving in water (+)-(4R,5S,6S)-6-[(1R)-1-hydroxyethyl]-4-methyl-7-oxo-3[[(3S,5S)-5-(sulfamoylaminomethyl)pyrrolidin-3-yl]thio]-1-azabicyclo[3.2.0]hept-2-ene-2-carboxylic acid; and (B) depositing the crystal from an aqueous solution obtained in step (A).

(7) In another aspect, a method according to the present invention is a method for producing the crystal of (1), comprising the steps of:

(A) dissolving in water (+)-(4R,5S,6S)-6-[(1R)-1-hydroxyethyl]-4-methyl-7-oxo-3[[(3S,5S)-5-(sulfamoylaminomethyl)pyrrolidin-3-yl]thio]-1-azabicyclo[3.2.0]hept-2-ene-2-carboxylic acid;

(B') depositing the crystal from an aqueous solution obtained in step (A), wherein a diffraction pattern of the deposited crystal in powder X-ray diffraction has main peaks at diffraction angles (2θ)=6.78, 6.96, 15.74, 17.92, 21.16, 23.56, and 25.80 (degrees); and (C) drying the crystal obtained in step (B').

Figure 1:
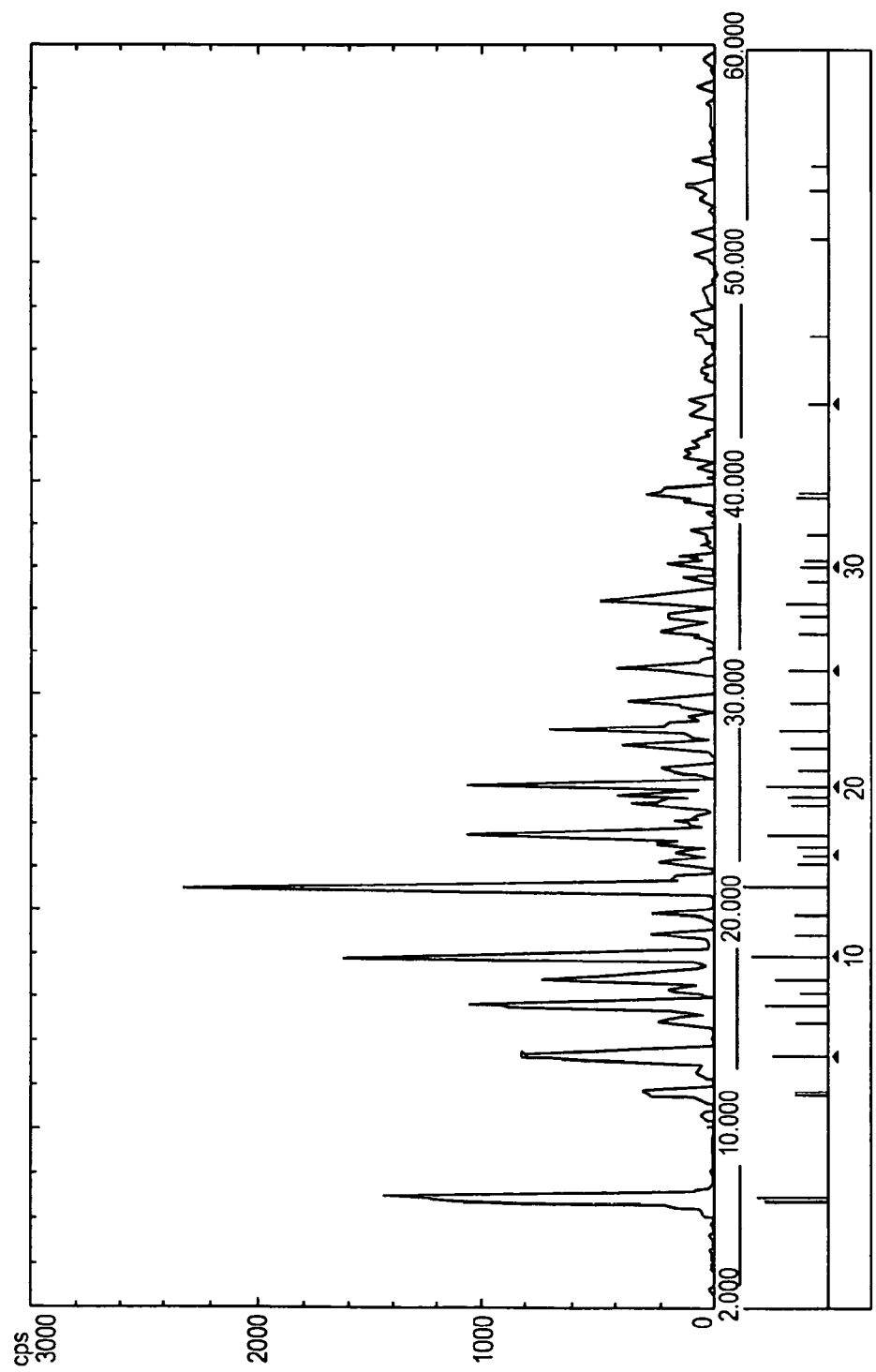
FIG. 1 shows a result of powder X-ray diffraction measurement for a type III crystal obtained in Example 1.

BEST MODE FOR CARRYING OUT THE INVENTION (Embodiments of the Invention)
(Explanation of S-4661)

The compound (+)-(4R,5S,6S)-6-[(1R)-1-hydroxyethyl]-4-methyl-7-oxo-3[[(3S,5S)-5-(sulfamoylaminomethyl)pyrrolidin-3-yl]thio]-1-azabicyclo[3.2.0]hept-2-ene-2-carboxylic acid (S-4661) is a pyrrolidylthiocarbapenem derivative. S-4661 is useful as an antimicrobial drug, and is orally or parenterally administered. This compound has broad spectrum of antibacterial activity and is effective against any gram-positive and gram-negative bacteria.

A crystal of the above-described S-4661 may be an inner salt crystal. The inner salt crystal of S-4661 is believed to have a betaine structure represented by a formula below.

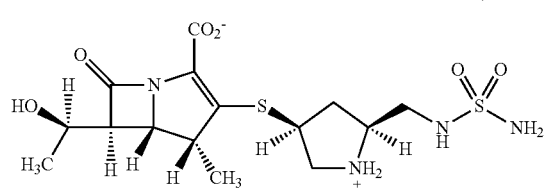

(Formula 2)

Such an inner salt crystal is more preferable since the crystal is in a pure form which contains no counterions other than the component of interest, unlike a Na salt or the like.

Results of powder X-ray diffraction measurement revealed that two new different types of S-4661 crystal forms exist. These two types of crystal form are hereinafter referred to as type III and type IV, respectively. The type III crystal and the type IV crystal are identified by their characteristic peaks obtained in powder X-ray diffraction. These crystals may be hydrates. Preferably, the type III crystal is a dihydrate and the type IV crystal is a monohydrate.

Diffraction angles (2θ) of characteristic main peaks of each crystal are indicated below.

Type III: diffraction angle (2θ)=6.78, 6.96, 15.74, 17.92, 21.16, 23.56, and 25.80 (degrees).

Type IV: diffraction angle (2θ)=13.04, 14.98, 15.88, 16.62, 20.62, 21.06, 22.18, 23.90, 26.08, 28.22 and 28.98 (degrees) (conditions for measurement of X-ray diffraction: CuKα ray, 1.54 Angstroms (monochromator), tube voltage 40 kV, tube current 40 mA).

When the crystal of the present invention is measured by X-ray diffraction, measurement error may occur in peaks to some extent depending on a measurement apparatus or measurement conditions. Specifically, for example, a measurement error of about ±0.2 may occur in the value of 2θ. Even when a very high-precision equipment is used, a measurement error of about ±0.1 may occur. Therefore, measurement error should be considered in identifying each crystal structure. Note that even when measurement error in X-ray diffraction is considered, the above-described characteristic peaks of the type I to type IV crystals in X-ray diffraction are absolutely different from one another. Therefore, X-ray diffractometry can be used to easily confirm the difference between the crystals of the present invention and other crystals.

Production of these crystals of S-4661 is a novel finding. The stability of the type III and type IV crystals is higher than that of the conventional type I and type II crystals. Therefore, the type III and IV crystals are more preferable than the type I and II crystals. Comparing the type III with the type IV, the stability of the type IV crystal is higher than that of the type III crystal. Therefore, the type IV crystal is more preferable than the type III crystal.

(Synthesis Method of S-4661)

S-4661 can be synthesized by conventionally known methods. For example, a method disclosed in Japanese Laid-Open Publication No. 5-294970 is available. Specifically, for example, 4-hydroxypyrrolidin-2-carboxylic acid or a derivative thereof is employed as a starting material. The steps comprises converting a hydroxyl group at position 4 of the 4-hydroxypyrrolidin-2-carboxylic acid derivative to a mercapto group; converting a carboxy group at position 2 to a hydroxymethyl group; converting a hydroxyl group of the hydroxymethyl group directly to sulfamide, or converting to an amino group and thereafter further converting to sulfamoyl; and optionally removing a protecting group Y1, can prepare the pyrrolidine derivative. The order of the steps can be changed, as desired. Position 4 of a pyrrolidine ring of the resultant pyrrolidine derivative may be optionally deprotected to a SH group. Thereafter, the pyrrolidine derivative is reacted with a carbapenem derivative to obtain a pyrrolidyl carbapenem derivative.

(Production Method of Crystals)

The crystal of S-4661 of the present invention may be obtained by a method of recrystallization or the like.

In one embodiment, the type III crystal of the present invention is obtained by recrystallization from water.

In one embodiment, the type IV crystal of the present invention is obtained by drying the type III crystal.

(Production Method of Type III Crystal)

The type III crystal of S-4661 can be obtained by, for example, crystallizing S-4661 synthesized by the above-described method from solution. Specifically, for example, S-4661 is crystallized from an organic solvent (e.g., alcohol, acetone, acetonitrile, and tetrahydrofuran), water, or a mixture thereof. Preferably, water alone is used as a solvent. Crystals are preferably deposited from substantially pure water containing no inorganic ions or the like. Examples of alcohol which may be used herein include methanol, ethanol, isopropanol, and isobutanol. When a mixed solvent of an organic solvent and water is used, the mixture ratio of water/organic solvent is preferably 1:0.5 to 1:100 (v/v).

In order to obtain the type III crystal, S-4661 is dissolved in preferably water, or the above-described mixed solvent of water and an organic solvent to prepare S-4661 solution. The concentration of the S-4661 solution is preferably about 5 to 40% by weight. In order to deposit a crystal of S-4661 from the solution, any crystallizing operation, such as cooling and/or stirring, or the like can be performed. Preferably, the solution is stirred while being cooled at about 0 to 10° C. to obtain a crystal of S-4661.

The type III crystal may be obtained as a single crystal by controlling crystallization conditions. For example, the type III crystal can be obtained by crystallizing S-4661 from water or a water/ethanol system. Preferably, the type III crystal is crystallized from water.

Here, when a seed crystal is not employed, a crystal of types other than type III may be deposited. For example, the type I crystal or the type II crystal may be deposited. Therefore, it is preferable to employ a seed crystal in order to selectively and efficiently deposit the type III crystal.

After crystallization from solution, the crystal is optionally dried. As such a drying method, conventionally known drying methods may be employed. For example, a drying method under reduced pressure using an aspirator or the like can be used. Specific drying conditions are, for example, as follows. The temperature is preferably 10° C. to 50° C., more preferably 15° C. to 40° C., and more preferably room temperature. The pressure is, for example, preferably 10 to 300 mmHg, more preferably 0 to 100 mmHg, more preferably 0 to 50 mmHg, and even more preferably 10 to 40 mmHg. The drying time is, for example, preferably 1 minute to 1 hour, more preferably 2 to 30 minutes, and even more preferably 5 to 20 minutes.

The moisture content of the type III crystal is not necessarily constant, but depends on the drying conditions and storage conditions. Preferably, the type III crystal is a dihydrate. The amount of organic solvent remaining in the crystal is not constant, varying depending on the crystallization method, drying conditions, and the like.

As with other crystals, the type III crystal may be preferably used as a material for pharmaceutical preparations. Moreover, as described below, the type III crystal can be used as an intermediate to easily produce the type IV crystal. Therefore, the type III crystal is very useful as an intermediate for production of the type IV crystal.

(Production Method of Type IV Crystal)

The type IV crystal can be easily obtained preferably by drying the above-described type III crystal. As the drying method, conventionally known drying methods may be adopted. Preferably, drying is conducted by application of heat and reduced pressure. Specifically, for example, the temperature is preferably 20° C. to 100° C., more preferably 30° C. to 70° C., and even more preferably 40° C. to 60° C. Further, the pressure is preferably, for example, 0 to 100 mmHg, more preferably 0 to 30 mmHg, even more preferably 0 to 20 mmHg, and particularly preferably 0 to 10 mmHg. The drying time is preferably, for example, 1 to 20 hours, more preferably 2 to 15 hours, and even more preferably 5 to 10 hours.

The moisture content of the type IV crystal is not necessarily constant, but depends on drying conditions and storage conditions. However, preferably, the type IV crystal is a monohydrate. The amount of organic solvent remaining in the crystal varies depending on the crystallization method, drying conditions, and the like, i.e., it is not constant. Note that the type IV crystal is preferably isolated as a monohydrate by drying a dihydrate type III crystal.

Thus, according to the present invention, a crystal of S-4661 having excellent crystal storage stability and a high industrial utility value is obtained.

(Medicaments Containing the Crystals of the Present Invention)

The crystals of the present invention can be employed as preparations for any medicament applications in which pyrrolidylthiocarbapenem derivatives have been conventionally used. Particularly, the crystals of the present invention are useful as antimicrobial drugs.

The preparation of the present invention may contain either of the above-described two crystals (i.e., the type III crystal and the type IV crystal) alone or a mixture thereof. When the preparation of the present invention contains the mixture of the two crystals, the crystals may be contained at an arbitrary mixture ratio. The type IV crystal is superior to the type III crystal in terms of storage stability. Therefore, the type IV crystal is more preferably used.

When a composition containing a crystal of the present invention is administered as an antimicrobial drug, a route of the administration is oral or parenteral. Examples of the dosage form include injections (ampoules, vials, solutions, suspensions, and the like for intravenous, intramuscular, drip, and hypodermic injections), external agents, topically administered agents (ear drops, nose drops, eye drops, ointments, emulsion, spray agents, suppositories, and the like), and orally administered agents. Particularly, the injection can be prepared using a powder filling preparation or a lyophilized preparation containing the crystal of the present invention.

The above-described preparations may contain an appropriate excipient, an auxiliary agent, a stabilizer, a wetting agent, an emulsifier, and other additives, depending on the dosage form. These have to be substances which can be pharmaceutically and pharmacologically utilized and have no influence on pyrrolidylthiocarbapenem derivatives. For example, the oral preparations may contain lactose, stearic acid, magnesium stearate, clay, sucrose, cornstarch, talc, gelatin, agar, pectin, peanut oil, olive oil, cacao butter, ethylene glycol, tartaric acid, citric acid, fumaric acid, and the like. The parenteral preparations may contain a solvent (alcohol, buffer, methyl oleate, water, and the like), a buffer solution, a dispersing agent, an auxiliary dissolving agent, a stabilizer (methyl p-hydroxybenzoate or ethyl p-hydroxybenzoate, sorbic acid, and the like), an absorbefacient (a mono- or dioctanate of glycerin), an antioxidant, a perfume, an analgesic, a dispersing agent, an adverse effect inhibitor, an action potentiator (an agent for regulating absorption and elimination, an inhibitor for enzyme decomposition, a β-lactamase inhibitor, other antimicrobial drugs), and the like.

The dose of the crystal of pyrrolidylthiocarbapenem derivative of the present invention varies depending on the age of a patient, the type and state of the disease, the type of compound used, and the like. In general, the daily dose falls within the range between 1 mg/patient (external application) and about 4000 mg/patient (intravenous injection). More than or equal to such an amount may be administered, if necessary. For treatment of infectious diseases, the crystal of the present invention is administered, for example, several times per day where a dose is 1 mg (external application), and 2 to 4 times per day where a dose is 1000 mg (intravenous injection).

When the crystal of pyrrolidylthiocarbapenem derivative of the present invention is used as an antimicrobial drug, target bacteria are any bacteria which are tackled by conventional pyrrolidylthiocarbapenem derivatives. It exhibits strong antimicrobial activity against both gram-positive bacteria and gram-negative bacteria.

EXAMPLES

Example 1

Production Method of Type III Crystal

Crude S-4661 (20.0 g) was added to ion-exchanged water (360 ml) and dissolved by heating to about 50 to 55° C., followed by filtration of the solution through a filtering instrument coated with activated carbon (600 mg) while maintaining a temperature of at least 50° C. After the filtrate was cooled to 15 to 20° C., a seed crystal of the type III crystal (20 mg) was put into the solution and stirred for about 120 minutes to deposit a crystal. Further, the crystal was cooled to 0 to 5° C. and aged for 2 hours. Isopropyl alcohol (200 ml) was poured into the solution over about 1 hour. Thereafter, the crystal was further deposited and aged at 0 to 5° C. for 2 hours and further overnight at the same temperature. The crystal was then filtered out. The resultant crystal was washed with 80% isopropyl alcohol water (40 ml), followed by drying under reduced pressure (20 to 30 mmHg) with an aspirator using tap water at room temperature for about 10 minutes to obtain the type III S-4661 crystal (18.1 g)(recovery rate: 90.5%).

A result of powder X-ray diffraction measurement for the resultant crystal is shown in FIG. 1. For the resultant crystal, the diffraction pattern of powder X-ray diffraction had main peaks at diffraction angles (2θ)=6.78, 6.96, 15.74, 17.92, 21.16, 23.56, and 25.80 (degrees). Further, relatively low peaks were present at diffraction angles (2θ)=11.56, 11.74, 13.38, 14.90, 16.88, 18.92, 19.82, 22.18, 23.02, 24.96, 25.32, 26.52, 27.66, 28.40, 29.70, 31.26, 33.00, 34.40, 39.46 and 39.70 (degrees).

Elemental analysis: for $C_{15}H_{24}N_4O_6S_2.2H_2O$
    Theoretical values: C39.46, H6.18, N12.27, S14.05
    Analytical values: C39.53, H6.14, N12.40, S14.06
    Moisture content
    Theoretical value (dihydrate): 7.89%
    Karl Fischer moisture meter (KF)
    measured value: 7.74%
    Melting point: 173° C. (decomposition).

Example 2

Production Method of Type IV Crystal

Figure 2:
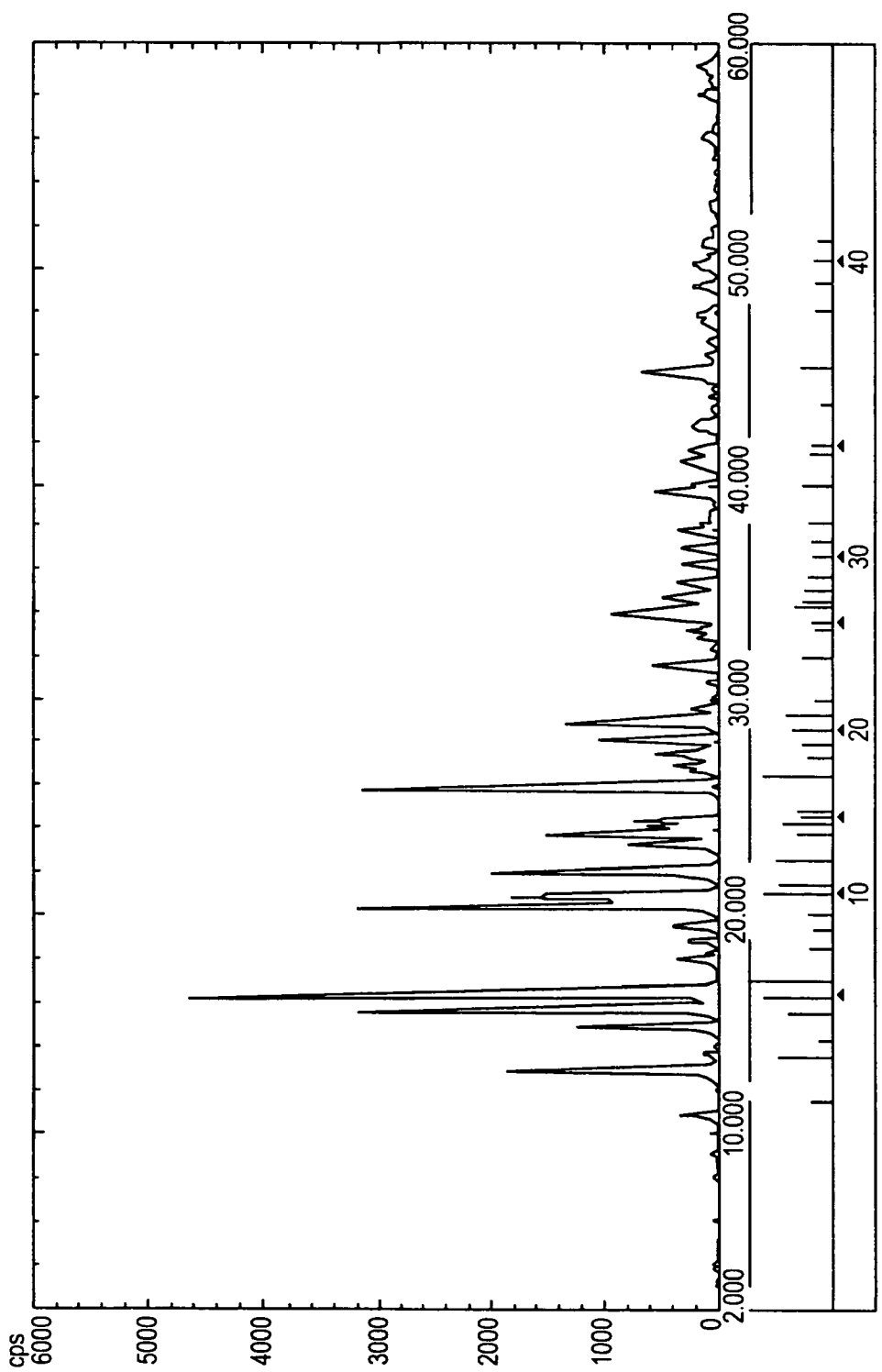
FIG. 2 shows a result of powder X-ray diffraction measurement for a type IV crystal obtained in Example 2.

The type III crystal (5.0 g) obtained in the above-described Example 1 was spread on a glass petri dish, and allowed to stand at 50° C. under reduced pressure (0 to 5 mmHg) for about 7 hours for drying. Thus, type IV crystal (4.8 g) was obtained (recovery rate: 96.0%). A result of powder X-ray diffraction measurement of the resultant crystal is shown in FIG. 2. The diffraction pattern of the resultant crystal in powder X-ray diffraction had main peaks at diffraction angles (2θ)=13.04, 14.98, 15.88, 16.62, 20.62, 21.06, 22.18, 23.90, 26.08, 28.22 and 28.98 (degrees). Further, relatively low peaks were present at diffraction angles (2θ)=23.42, 24.20, 24.46, 27.54, 31.70, 34.14, 34.36, 34.92, 39.82 and 45.24 (degrees).

Elemental analysis: for $C_{15}H_{24}N_4O_6S_2.H_2O$
    Theoretical values: C41.08, H5.98, N12.78, S14.62
    Analytical values: C41.01, H5.92, N12.83, S14.56
    Moisture content
    Theoretical value (monohydrate): 4.11%
    Karl Fischer moisture meter (KF)
    measured value: 4.28%
    Melting point: 173° C. (decomposition).

Example 3

Reproducibility of Production of Type III Crystal

A repeat experiment was conducted in order to confirm the reproducibility of the above-described Example 1.

The diffraction pattern of a resultant type III crystal in powder X-ray diffraction had main peaks at diffraction angles (2θ)=6.62, 13.04, 15.44, 16.58, 17.64, 20.88, 23.26, 25.02 and 25.52 (degrees).

Example 4

Reproducibility of Production of Type IV Crystal

A repeat experiment was conducted in order to confirm the reproducibility of the above-described Example 2.

Figure 3:
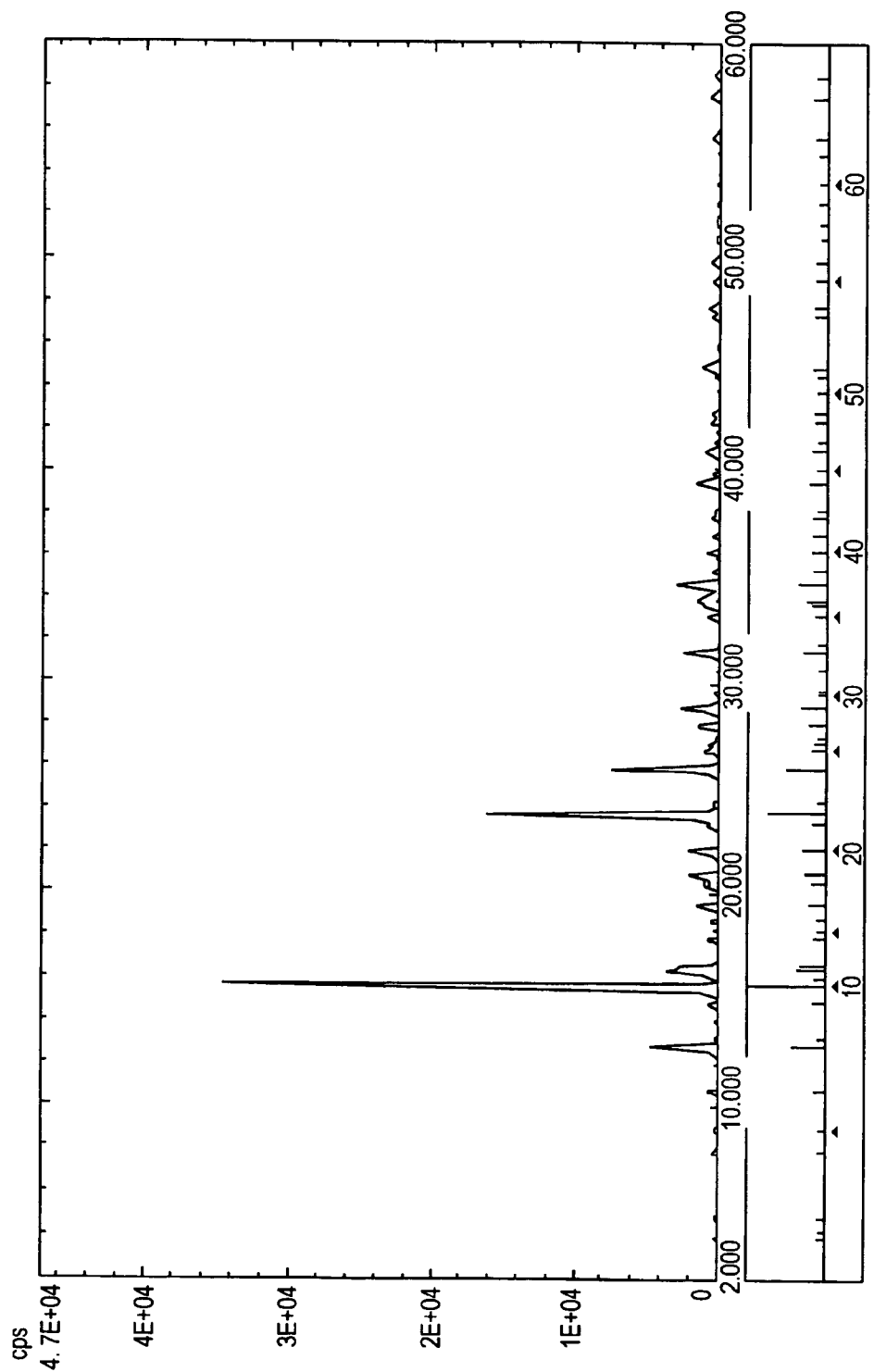
FIG. 3 shows a result of powder X-ray diffraction measurement for a type IV crystal obtained in Example 4.
Figure 4:
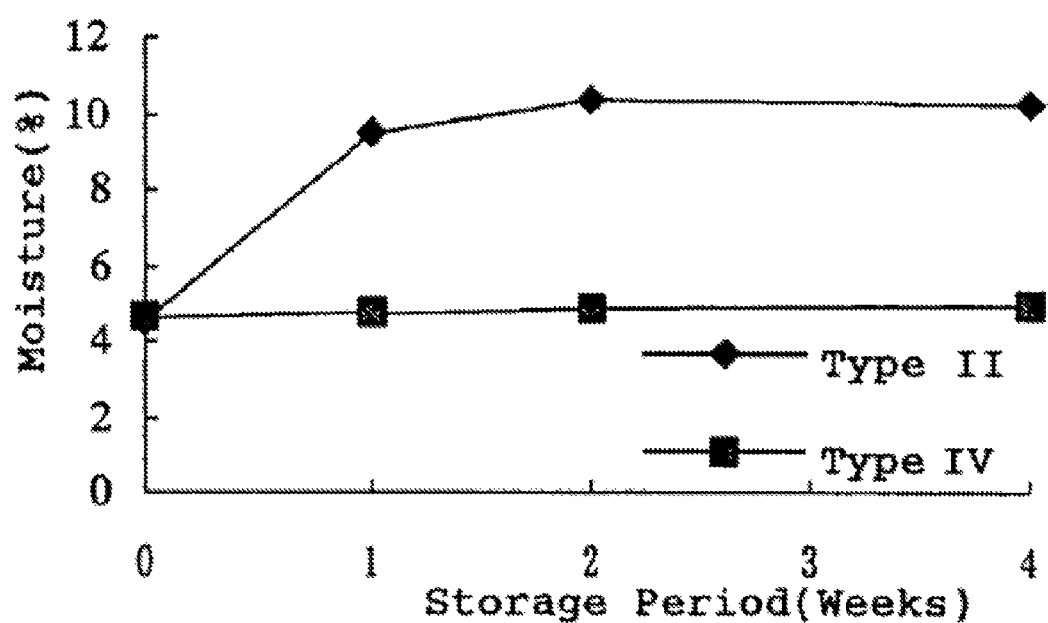
FIG. 4 shows a result of moisture measurement for type II and type IV crystals as determined in Example 4.
Figure 5:
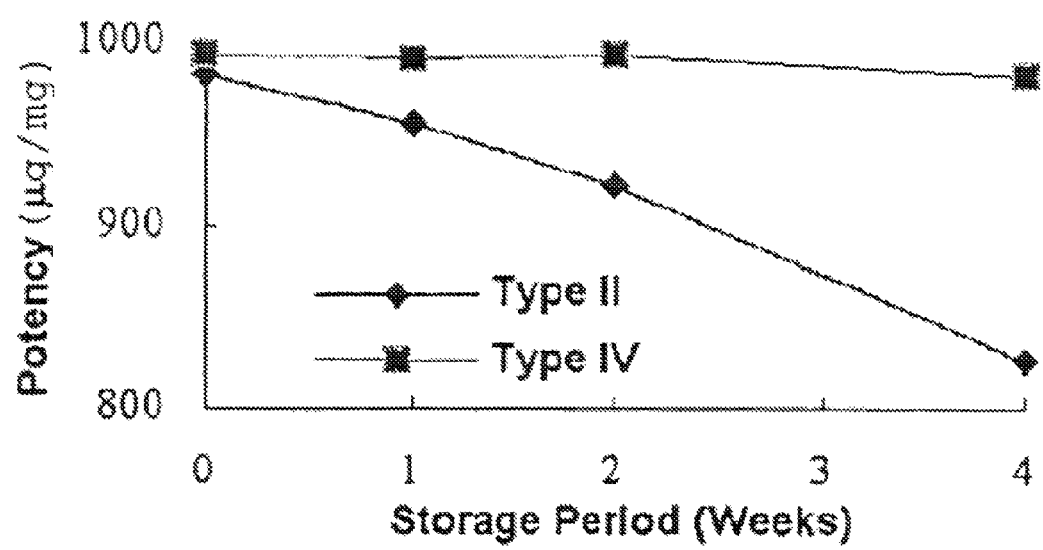
FIG. 5 shows a result of potency measurement for type II and type IV crystals as determined in Example 4.

The type III crystal obtained in the above-described Example 3 was used to prepare type IV crystal in accordance with the method of the above-described Example 2. A result of a resultant crystal in powder X-ray diffraction measurement is shown in FIG. 3.

The diffraction pattern of the resultant type IV crystal in powder X-ray diffraction had main peaks at diffraction angles (2θ)=12.90, 15.74, 16.48, 23.78, and 25.92 (degrees).

Elemental analysis: for $C_{15}H_{24}N_4O_6S_2.H_2O$
    Theoretical value: C41.08, H5.98, N12.78, S14.62
    Analytical value: C41.93, H6.03, N13.02, S14.52
    Moisture content
    Theoretical value (monohydrate): 4.11%
    Karl Fischer moisture meter (KF)
    measured value: 4.3%

(Assessment of Stability)

The storage stability of the thus-obtained crystal of the present invention was assessed. As a result, it was found that the type III crystal of the present invention has excellent storage stability as compared to conventional type I or II crystals, and the type IV crystal of the present invention has more excellent storage stability.

Hereinafter, a result of evaluation of comparing the stability of the crystals of the present invention with that of a conventional crystal (type II crystal) is specifically shown.

The stability of type II crystal of S4661 (conventional crystal) was compared with that of the type IV crystal obtained in the above-described Example 4.

Firstly, the testing method will be described.

Storage conditions were 40° C. and 75% RH. The periods of time for storage were 1 week, 2 weeks and 1 month. During these storage periods, samples were stored in opened petri dishes.

After storage in this manner, the moisture and potency of each sample were measured.

The moisture was measured according to REQUIREMENT FOR ANTIBIOTIC PRODUCTS OF JAPAN General Tests MOISTURE DETERMINATION II Water determination. Note that Karl Fischer formamide methanol mixture II was used as the solvent.

A potency test was conducted by the following method. About 0.025 g of each of the type IV crystal obtained in Example 4 and type II crystal and a standard product of S-4661 was precisely measured. Each sample was dissolved in water to precisely 100 mL. 10 mL of each solution was precisely measured, to which 5 ml of internal standard solution was added. As the internal standard solution, aqueous acetaminophen solution (concentration 1/20000:1 g of acetaminophen in 20000 ml of the solution) was used. Thereafter, water was added to each solution to 50 mL. Solutions prepared from the type IV or II crystals were used as sample solutions. A solution prepared from a standard product of S-4661 was used as a standard solution. 10 μL of each of the sample solutions and the standard solution were subjected to liquid chromatography under the following conditions. For the sample solution, the ratio $Q_T$ of the peak area of S-4661 to the peak area of the internal standard substance was obtained. For the standard solution, the ratio $Q_S$ of the peak area of S-4661 to the peak area of the internal standard substance was obtained.

Conditions for Operation

Detector: ultraviolet absorptiometer (measurement wavelength: 240 nm)

Column: a stainless steel tube having an inner diameter of about 4.6 mm and a length of about 15 cm was filled with 5 μm of octadecylsilylated silica gel for liquid chromatography (L-column ODS).

Column temperature: a constant temperature of around 25° C.

Mobile phase: 2 mmol/L phosphate buffer pH 5.8/acetonitrile mixture (191:9)

Flow rate: Flow rate was adjusted so that the retention time of S-4661 was about 8 to 9 minutes (about 1 mL/min).

Selection of column: 10 μL of standard solution was used and the operation was conducted under the above-described conditions. A column, which elutes S-4661 and the internal standard substance in this order and has a resolution between S-4661 and the internal standard substance of at least 3, was used.

Potencies were calculated by the following expression.

Potency per 1 mg of the type IV or II crystal (μg/mg) =

$$\frac{Q_T}{Q_S} \times \frac{\text{Weight (mg) of Standard product of } S-4661 \text{ (titer)}}{\text{Weight (mg) equivalent to dehydrated product of crystal}} \times 1000$$

The obtained test results are shown below.

| Result of Moisture Measurement | | |
|---|---|---|
| Storage period | Type II | Type IV Unit (%) |
| Initial time | 4.56 | 4.62 |
| 1 week | 9.51 | 4.79 |
| 2 weeks | 10.36 | 4.89 |
| 1 month | 10.31 | 4.99 |

In the case of the type II crystal, it can be understood that the moisture increased over time, and the moisture became constant after about two weeks (about 10%). On the other hand, in the case of the type IV crystal, the initial amount of moisture was maintained for a long period of time. Therefore, it was confirmed that whereas the type II crystal absorbs moisture, the type IV crystal absorbs substantially no moisture.

| Result of Potency Measurement | | |
|---|---|---|
| Storage period | Type II | Type IV Unit (μg/mg) |
| Initial time | 983.2 | 993.3 |
| 1 week | 956.2 | 990.8 |
| 2 weeks | 923.0 | 992.4 |
| 1 month | 826.4 | 981.5 |

In the case of the type II crystal, it was confirmed that the potency decreased over time. In the case of the type IV crystal, no significant change was detected.

As can be seen from the moisture measurement result, the type II crystal has moisture absorption ability. Therefore, a procedure of weighing the type II crystal has to be performed in a dry chamber. Other procedures have to be conducted under constant humidity. On the other hand, the type IV crystal is not observed to absorb moisture in an environment of 40° C. and 75% RH and therefore above-described procedures can be omitted. Other test results revealed that the type IV crystal was more stable than the type II crystal.

(Assessment of Preparations)

Preparations employing the crystal of the present invention are assessed as follows. 250 mg of type IV crystal is dissolved in 100 mL of physiological saline to prepare an injection. If the efficacy of the injection is assessed, it is confirmed that the type IV crystal has efficacy similar to that of the conventional type I and II crystals.

INDUSTRIAL APPLICABILITY

Effects of the Invention

According to the present invention, novel crystals having excellent storage stability and a production method thereof are provided. Further, according to the present invention, novel crystals which can be used in powder filling preparations and the like and a production method thereof are provided.

The invention claimed is:

1. A crystal of a dihydrate of (+)-(4R,5S,6S)-6-[(1R)-1-hydroxyethyl]-4-methyl-7-oxo-3[[(3S,5S)-5-(sulfamoylaminomethyl)pyrrolidin-3-yl]thio]-1-azabicyclo[3.2.0]hept-2-ene-2-carboxylic acid having a powder X-ray diffraction pattern comprising peaks at diffraction angles (2θ) of about 6.62, 13.04, 15.44, 16.58, 17.64, 20.88, 23.26, 25.02 and 25.52 (degrees), wherein the powder X-ray diffraction pattern is obtainable using Cu Kα ray, 1.54 Angstroms (monochromater), tube voltage 40 kV, and tube current 40 mA.

2. A method for producing a crystal according to claim 1, comprising the steps of:
    (A) dissolving (+)-(4R,5S,6S)-6-[(1R)-1-hydroxyethyl]-4-methyl-7-oxo-3[[(3S,5S)-5-(sulfamoylaminomethyl)pyrrolidin-3-yl]thio]-1-azabicyclo[3.2.0]hept-2-ene-2-carboxylic acid or a hydrate thereof in water;
    (B) depositing crystals from the aqueous solution obtained in step (A);
    (C) determining the powder X-ray diffraction pattern of the crystals deposited in step (B); and
    (D) selecting a crystal having a powder X-ray diffraction pattern comprising peaks at diffraction angles (2 θ) of about 6.62, 13.04, 15.44, 16.58, 17.64, 20.88, 23.26, 25.02 and 25.52 (degrees), wherein the powder X-ray diffraction pattern is obtainable using Cu Kα ray, 1.54 Angstroms (monochromator), tube voltage 40 kV, and tube current 40 mA.

3. A method for producing a crystal of a dihydrate of (+)-(4R,5S,6S)-6-[(1R)-1-hydroxyethyl]-4-methyl-7-oxo-3 [[(3S,5S)-5-(sulfamoylaminomethyl)pyrrolidin-3-yl]thio]-1-azabicyclo[3.2.0]hept-2-ene-2-carboxylic acid, said crystal having a powder X-ray diffraction pattern comprising peaks at diffraction angles (2θ) of about 6.62, 13.04, 15.44, 16.58, 17.64, 20.88, 23.26, 25.02 and 25.52 (degrees), wherein the powder X-ray diffraction pattern is obtainable using Cu Kα ray, 1.54 Angstroms (monochromator), tube voltage 40 kV, and tube current 40 mA, said method comprising the steps of:

(A) dissolving (+)-(4R,5S,6S)-6-[(1R)-1-hydroxyethyl]-4-methyl-7-oxo-3[[(3S,5S)-5-(sulfamoylaminomethyl) pyrrolidin-3-yl]thio]-1-azabicyclo[3.2.0]hept-2-ene-2-carboxylic acid or a hydrate thereof in water;

(B) placing a seed crystal produced according to claim 2 or recited in claim 1 in the aqueous solution obtained in step (A);

(C) depositing crystals from the seeded aqueous solution obtained in step (B); and (D) isolating the crystals formed in step (C).

* * * * *